(12) United States Patent
Fischer et al.

(10) Patent No.: US 6,270,344 B1
(45) Date of Patent: Aug. 7, 2001

(54) DENTAL HANDPIECE TUBING COUPLER AND RELATED SYSTEMS

(75) Inventors: Dan E. Fischer; Bruce S. McLean, both of Sandy; Richard Kim Bleiweiss, Bountiful, all of UT (US)

(73) Assignee: Ultradent Products, Inc., SouthJordan, UT (US)

( * ) Notice: Subject to any disclaimer, the term of this patent is extended or adjusted under 35 U.S.C. 154(b) by 0 days.

(21) Appl. No.: 09/602,220

(22) Filed: Jun. 23, 2000

(51) Int. Cl.[7] ........................................... A61C 1/08
(52) U.S. Cl. .................................................. 433/126
(58) Field of Search ................................................ 433/126

(56) References Cited

U.S. PATENT DOCUMENTS

| | | | |
|---|---|---|---|
| 4,303,392 | * 12/1981 | Rollofson | 433/126 |
| 4,470,812 | * 9/1984 | Martens et al. | 433/126 X |
| 5,039,304 | * 8/1991 | Heil | 433/126 |
| 5,476,379 | * 12/1995 | Disel | 433/29 |
| 5,749,726 | * 5/1998 | Kinsel | 433/126 X |

* cited by examiner

Primary Examiner—Nicholas D. Lucchesi
(74) Attorney, Agent, or Firm—Workman, Nydegger & Seeley

(57) ABSTRACT

Coupler and system for dental handpiece tubing that permit the extension of commercially available tubing and also the connection of commercially available tubing to auxiliary device tubing. The coupler comprises a body for detachable connection with a variety of tubing terminal assemblies, and at least one lumen for establishing fluid communication between the lumens of the pieces of tubing to be linked by the coupler. Different embodiments of the coupler are provided with blind ports and with a plurality of lumen for channeling fluid flows and for channeling specialized elements, such as elements that cooperate with imaging, illumination, irradiation devices and probes.

42 Claims, 9 Drawing Sheets

DENTAL HANDPIECE TUBING COUPLER AND RELATED SYSTEMS

BACKGROUND OF THE INVENTION

1. The Field of the Invention

This invention relates to dental handpiece tubing couplers. More particularly, this invention relates to couplers for tubing used in dental handpieces, where the tubing has at least one lumen for channeling fluid, and the coupler can be configured for use with multi-lumen dental handpiece tubing.

2. Related Art

One of the primary uses for dental handpieces is drilling cavities in teeth. The drilling mechanism in these handpieces is a turbine-operated drill powered by a supply of fluid. This fluid is delivered through a conduit within the handpiece from a lumen of a tubing. The lumen of the tubing provides the attachment of the dental handpiece to at least the source of the fluid that is needed to power the turbine.

In the simplest handpiece systems, only one conduit and only one lumen run through the handpiece and the tubing, respectively. More typically, the dental handpiece has a plurality of conduits which are in fluid communication with a plurality of corresponding lumens within and along the tubing. These conduits and lumens independently channel fresh air to power the turbine, exhaust air from the turbine, and additional fluid or fluids for cooling the drill. In these more sophisticated systems the tubing establishes a connection between the dental handpiece and the discharge point for the exhaust fluid and the sources of the different fluids.

In even more complex systems, additional conduits through the dental handpiece in communication with corresponding lumens along the tubing are used for housing probing, illuminating and/or imaging elements such as optical fibers. In these more complex systems the tubing establishes a connection between the dental handpiece and the probing, illuminating and/or imaging instruments.

In any case, the tubing that connects the dental handpiece with at least a source of fluid to power the turbine is a flexible tube which in most embodiments has a plurality of lumens. Furthermore, tubing with these characteristics is usually available to practitioners in fixed lengths with their ends properly fitted with attachment elements such as threaded assemblies or assemblies configured for compression fitting.

In some instances, however, practitioners need to lengthen the tubing without disassembling the tubing ends that are provided with attachment elements. Due to the cost of the tubing, it is expensive to replace tubing of insufficient length. In other instances, practitioners might want to force at least one of the fluids to run through an auxiliary device, such as a water filter. Modified tubing that is properly assembled with such an auxiliary device is convenient for its use by practitioners, provided that such modified tubing can easily be connected in a leak-proof fluid communication with existing unmodified tubing.

Whether the goal is to lengthen tubing or to connect unmodified tubing to other tubing that has been assembled with an auxiliary device, the final length of tubing reaching the dental handpiece should effectively provide the necessary leak-proof channels for the proper operation of the dental handpiece. However, the presence of attachment elements at the ends of different pieces of tubing often makes them incompatible for their direct connection, unless the attachment elements are disassembled and replaced, or some tubing is cut and refitted with the appropriate attachment element.

Accordingly, there is a need for a coupler that permits the connection of dental handpiece tubing provided with attachment elements at its ends, such that no disassembling of the attachment elements or cutting of tubing is required.

OBJECTS AND BRIEF SUMMARY OF THE INVENTION

The present invention has been developed in response to the present state of the art and, in particular, in response to problems and needs that have not been solved heretofore. It is an object of the present invention to provide detachable couplers for dental handpiece tubing and achieve with such couplers an effective leak-proof fluid communication between the connected pieces of tubing. It is also an object of the present invention to provide a dental handpiece tubing coupler that can be used for extending commercially available dental handpiece tubing. It is an additional object of the present invention to provide a dental handpiece tubing coupler that can be used for connecting auxiliary devices to commercially available dental handpiece tubing.

The present invention can be embodied by couplers of different cross sections and by couplers whose attachment elements have any one among a variety of configurations. The plurality of cross sections can advantageously be used for optimally arranging the lumens within each coupler. Furthermore, a plurality of cross sections can be advantageously used as distinguishing features among couplers that have different numbers of lumens or that have specialized lumens. The variety of attachment element configurations in embodiments of couplers according to this invention advantageously permit the use of couplers with a wide range of commercially available dental handpiece tubing, whether the ends of such tubing are manufactured with threaded or non-threaded attachment elements, and whether the attachment elements are generally circular or have other shapes.

The variety of shapes and configurations of the couplers of the present invention advantageously removes the need for the practitioner to cut tubing or perform involved assembly operations when a dental handpiece tubing is to be extended or some auxiliary device has to be connected to such tubing.

To achieve the foregoing objects, and in accordance with the invention as embodied and broadly described herein, couplers according to the present invention comprise a body with coupling terminals that are configured for detachable engagement with tubing assemblies. In addition, couplers according to the present invention comprise at least one coupler lumen extending through the body. This lumen has connectors at its ends that are configured for detachable leak-proof connection with at least one tubing lumen. When the ends of commercially available dental handpiece tubing are connected with a coupler according to the present invention, leak-proof fluid communication between the tubing lumens is established through the coupler lumen.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Same numbers used in different drawings label like features. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention is directed to dental handpiece tubing couplers with at least one lumen for channeling fluid. The couplers of this invention are used to establish a leak-proof fluid communication between pieces of tubing. When the tubing has a plurality of lumens, an embodiment of the coupler of this invention is used to establish leak-proof fluid communication between corresponding lumens in each tubing and also for providing an effective passage for any other specialized tubing lumen, such as a lumen that channels optical fibers. When the tubings that are to be connected to each other have different numbers of tubing lumens, embodiments of couplers of the present invention can be provided with blind ports for the lumen or lumens of one tubing that are not to find a corresponding connection with any lumen in the other connected piece of tubing.

FIGS. 1A–1D show views of commercially available dental handpieces and tubing that is typically used with such handpieces. These figures show a dental handpiece and tubing at different stages in the process of being connected to each other.

Figure 1A:
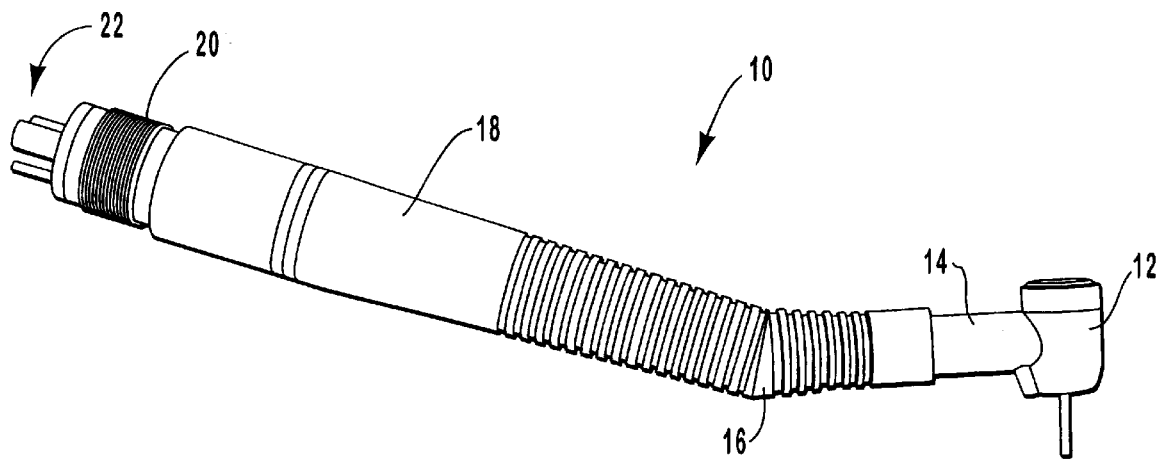
FIG. 1A shows a side view of a dental handpiece.

FIG. 1A shows a side view of a commercially available dental handpiece 10 with head element 12, neck element 14, elbow element 16, and cone element 18 ending with threaded attachment unit 20 from which a plurality of conduits 22 extend. Internal components in head element 12 and any motor housed in cone element 18 or in any other internal region of handpiece 10 typically receive fluids through conduits 22. Any exhaust fluid can be channeled away from dental handpiece 10 through one or several of conduits 22. Furthermore, one or several of conduits 22 can be used for channeling specialized elements such as optical fibers or any other elongated element that cooperates with imaging, illumination, and irradiation devices and probes.

Figure 1B:
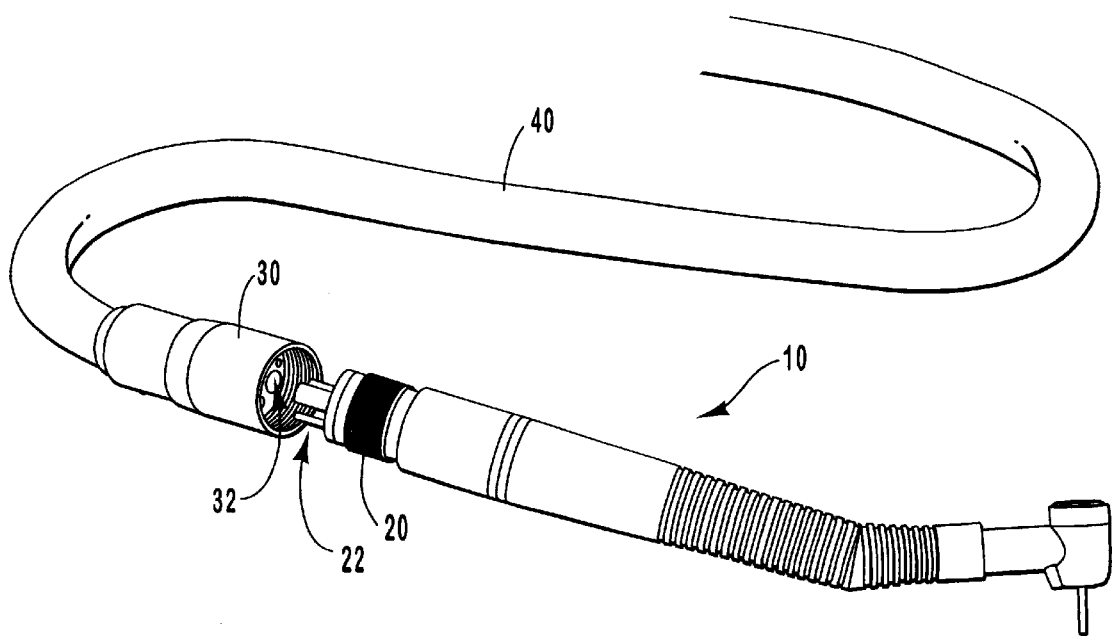
FIG. 1B shows a perspective view of a dental handpiece and tubing to be connected to the dental handpiece.

FIG. 1B shows dental handpiece 10 with its threaded attachment 20 next to internally threaded receiving assembly 30 of tubing 40. In most commercially available dental handpiece tubing, receiving assembly 30 is slidably mounted outside, around and generally coaxially with tubing 40.

Figure 1C:
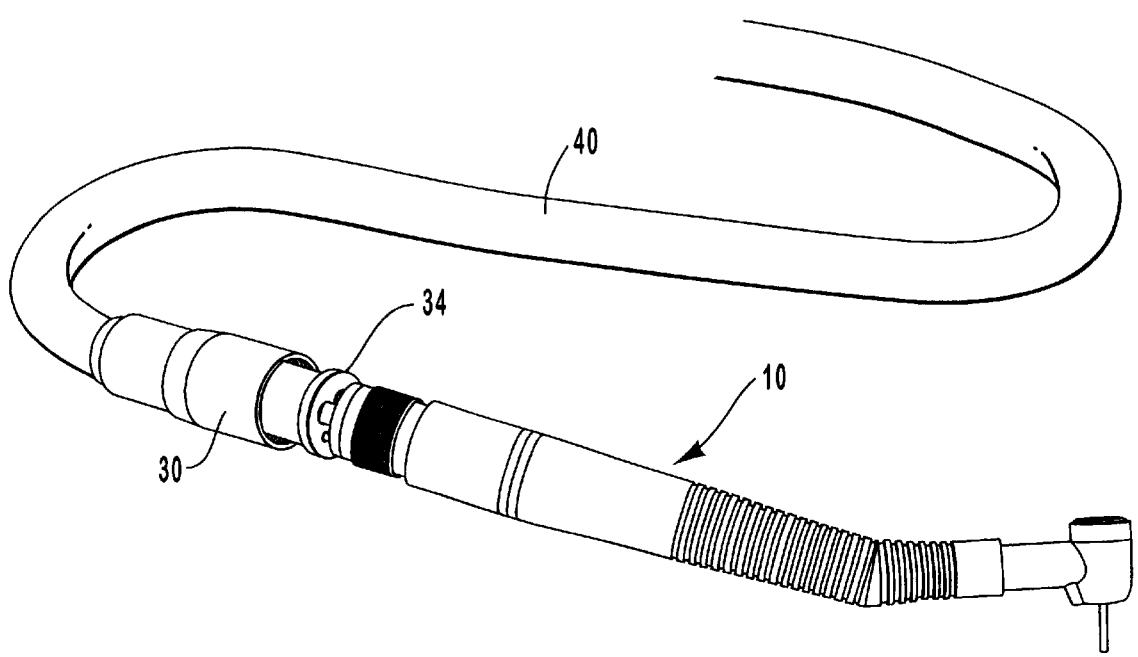
FIG. 1C shows a perspective view of a dental handpiece with its conduit ends partially inserted into the receiving lumens of the tubing.
Figure 1D:
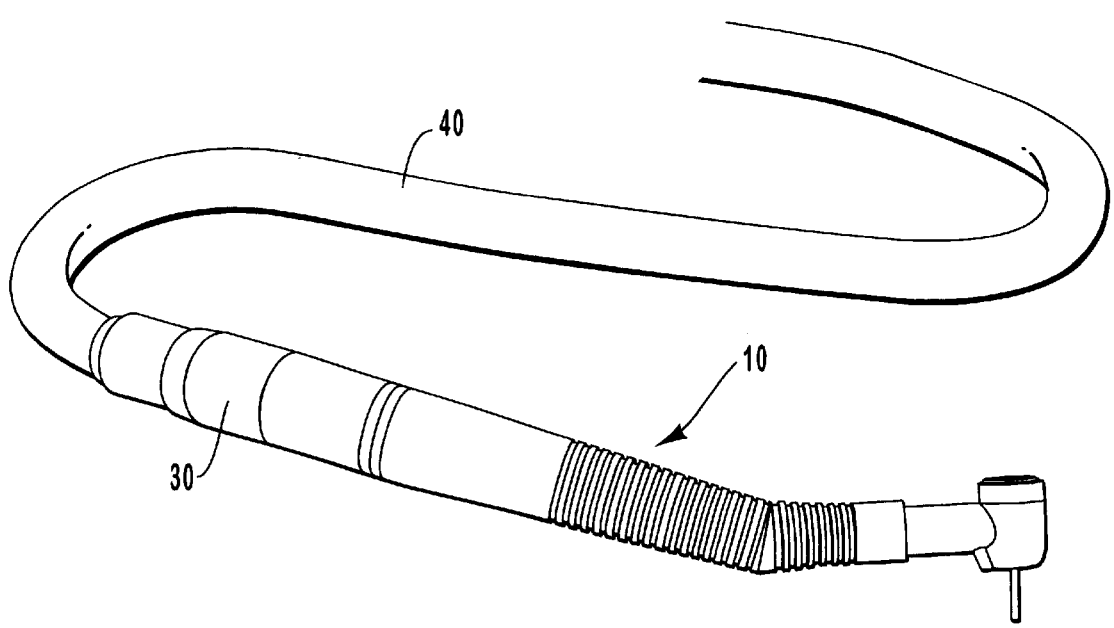
FIG. 1D shows a perspective view of the fully connected set of tubing and handpiece shown in disconnected configurations in FIGS. 1A–1C.

As shown in FIG. 1C, receiving assembly 30 can be slid along tubing 40 away from tubing end 34 that is to be connected to dental handpiece 10. Each one of conduits 22 can be connected to the corresponding lumens 32. Typically, each one of conduits 22 is received by a corresponding lumen 32 in a leak-proof fluid communication. Conduits 22 and lumens 32 so connected, however, could be dislodged or disconnected by pulling handpiece 10 or by some other action that could impart some torque or tension into the connection of conduits 22 to lumens 32. Dislodging this connection would cause the unacceptable leakage of any fluid circulating along conduits 22 and lumens 32. To avoid any such leakage, receiving assembly 30 is slid towards threaded attachment unit 20 after conduits 22 are connected to lumens 32, and receiving assembly 30 is then threadably engaged to threaded attachment unit 20 to secure the connection of dental handpiece 10 to tubing 40, as shown in FIG. 1D.

In most commercially available dental handpieces, the drill is actuated by air-driven turbines, in which case the tubing has at least one lumen for channeling the air to be delivered to the turbine, and at least one conduit that runs through the handpiece is connected to such lumen as shown in FIGS. 1A–1D. Dental handpiece tubing includes several types of tubing, such as the three-hole tubing known as Borden tubing, the four-hole tubing known as Midwest, the five-hole or six-hole tubing which is similar to the Midwest tubing and has respectively one or two fiber optic links.

Among these types, the more common tubing is the four-hole Midwest, which typically houses four cylindrical lumens extending longitudinally therewithin. Two of these four lumens usually have a larger diameter, and the remaining two lumens have smaller diameter. When the dental handpiece operates, one of the larger lumens channels air to power the turbine or turbines, whereas the other large tube channels away from the handpiece the exhaust air discharged from the turbine or turbines. The two smaller lumens typically channel fluids for cooling the drill in operation. One of such lumens channels water and the other channels air that is used to atomize the water upon delivery to the drill.

Because the distance from the source of the dental handpiece power fluid to the work area where the handpiece is used can vary depending on specific work environment requirements, additional extension tubing must sometimes be used. Furthermore, the use of an auxiliary device may be necessary. For example, the cooling water might require some physical or chemical treatment with the aid of an auxiliary device such as filter 50 shown in FIG. 2 and device 350 shown in FIG. 3A.

Figure 2:
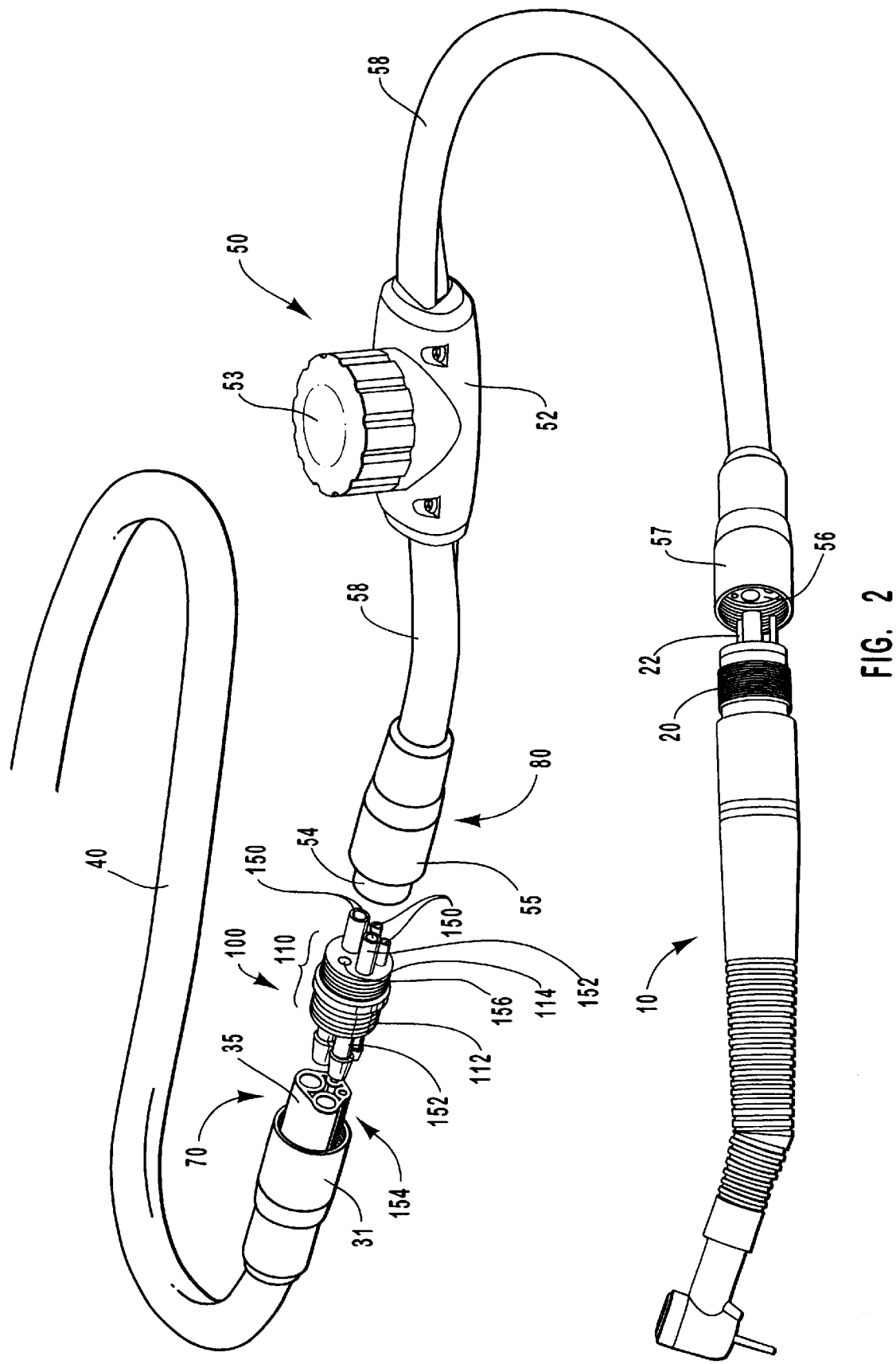
FIG. 2 shows a perspective view of a dental handpiece to be connected to one end of a filter tubing and a connector arranged between the ends of a tubing and a filter tubing.

Filter 50 shown in FIG. 2 is an example of an auxiliary device that is to be connected to the dental handpiece and to one end of commercially available dental handpiece tubing. An embodiment of a water filter such as filter 50 includes assembly 52 that provides a derivation of the water lumen extending within and along filter tubing 58 so that water can be filtered in the suitable filtering system. In the embodiment shown in FIG. 2, the filtering system is accessible by removing filter cap 53. Filter tubing 58 usually ends with receiving attachment elements such as filter tubing end 54 and threaded filter assembly 55 at one end, and circular filter tubing end 56 and threaded filter assembly 57 at the opposite end. Filter tubing end 54 and threaded filter assembly 55 are configured like filter tubing end 56 and threaded assembly 57, respectively, in the embodiment shown in FIG. 2.

Whether the practitioner needs to extend tubing 40 or to connect an auxiliary device, the necessary connections are to be performed with minimal or no waste of tubing and without requiring from the practitioner any inordinately laborious task. These connections, however, can become difficult or impossible to perform without dismounting and reassembling attachment elements because attachment elements at the ends of most commercially available tubing are receiving structures which cannot be directly connected to other receiving structures. For example, FIG. 2 shows attachment element 70 comprising compression fitting assembly 31 and non-circular tubing end 35, and attachment element 80 comprising threaded filter assembly 55 and filter tubing end 54. These two attachment elements cannot be connected directly to each other.

FIG. 2 shows an embodiment of the present invention depicted therein as coupler 100, which comprises body 110 with coupling terminals 112 and 114, and coupler lumens 150. Embodiments of the body of the coupler of this invention provide the structural framework for the coupler lumens and for the coupling terminals. Embodiments of coupler lumens according to the present invention provide the passages that permit the establishment of fluid communication between lumens in pieces of tubing that are to be connected with a specific embodiment of the coupler. The particular embodiment of the coupler shown in FIG. 2 comprises four coupler lumens 150. The embodiments of couplers shown in FIGS. 3A, 3B, and 5 also comprise four coupler lumens, and the embodiment of coupler shown in FIG. 6 comprises three coupler lumens and a fourth coupler lumen that is provided with a blind port.

Straight and generally cylindrical coupler lumens as shown in FIG. 2 are preferred embodiments of coupler lumens of this invention, but other embodiments of this invention have one or more non-straight lumens, such as curved lumens, branching lumens, and helically extending lumens. Other embodiments of this invention have tapered lumens. Furthermore, other embodiments of this invention have coupler lumens whose vertical cross section is non-circular, and these coupler lumens are preferred embodiments for matching similar non-circular lumens in the tubings to be connected. Straight coupler lumens, tapered lumens, non-straight coupler lumens, such as curved lumens, branching lumens, and helically extending lumens, and non-circular vertical cross-section lumens described hereinabove and equivalents thereof are examples of means for establishing fluid communication according to the present invention.

Body 110 as shown in FIG. 2 has a generally circular vertical cross section, which is the cross section in the plane perpendicular to coupler lumens 150. However, embodiments of the body of the coupler of this invention can have a variety of cross sections in addition to circular, such as polygonal, ellipsoidal, cross sections with an outer perimeter that comprises a combination of arcuate sides, and cross sections with an outer perimeter that comprises a combination of arcuate and rectilinear sides. The shapes of these cross sections can be used for identification purposes in addition to aesthetic preferences, so that couplers with different connection features have different body cross sections. For example, couplers for single-lumen tubing can have a circular body cross section, couplers for two-lumen tubing can have an ellipsoidal cross section, couplers for three-hole Boren tubing can have a triangular body cross section, couplers for four-hole Midwest tubing can have a square body cross section, couplers for five-hole fiber optic tubing can have a pentagonal body cross section, couplers for six-hole two-fiber-optic tubing can have a hexagonal body cross section, and couplers with blind ports for connecting two pieces of tubing that have different numbers of tubing lumens can have a body cross section with a perimeter comprising a combination of straight and arcuate sides, the number of arcuate sides being equal to the number of blind ports in the coupler. Although the central vertical cross section is non-circular in some embodiments of the coupler of the present invention, the coupling terminals such as coupling terminals 112 and 114 are shaped so that they can effectively attach to the available tubing attachment elements.

All of the embodiments of the coupler bodies described herein and equivalents thereof are examples of embodiments of means for detachably linking tubing assemblies according to the present invention. More particularly, coupler bodies with at least one lumen configured for the transmission of a fluid such as air and water are examples of embodiments of means for detachably linking tubing assemblies. As indicated above, the coupler body may also be configured for the transmission of a specialized signal such as the optical signal used in imaging systems. Another example of a specialized signal is the radiation used in irradiating devices. Coupler bodies configured for the transmission of a specialized signal in addition to a fluid are also examples of means for detachably linking tubing assemblies. More specifically, such coupler bodies are examples of means for detachably linking tubing assemblies to enable the transmission of fluids and specialized signals.

The arrangement of coupler lumens in the coupler body is such that the coupler lumen ends form a mating configuration with respect to the corresponding tubing elements. For example, the embodiment shown in FIG. 2 shows an arrangement of four coupler lumens 150 such that the four lumens are arranged parallel to one another, with the two upper lumens being the larger lumens for channeling water to and from the turbine and the two lower lumens are the smaller lumens for the drill cooling water and air.

Figure 3A:
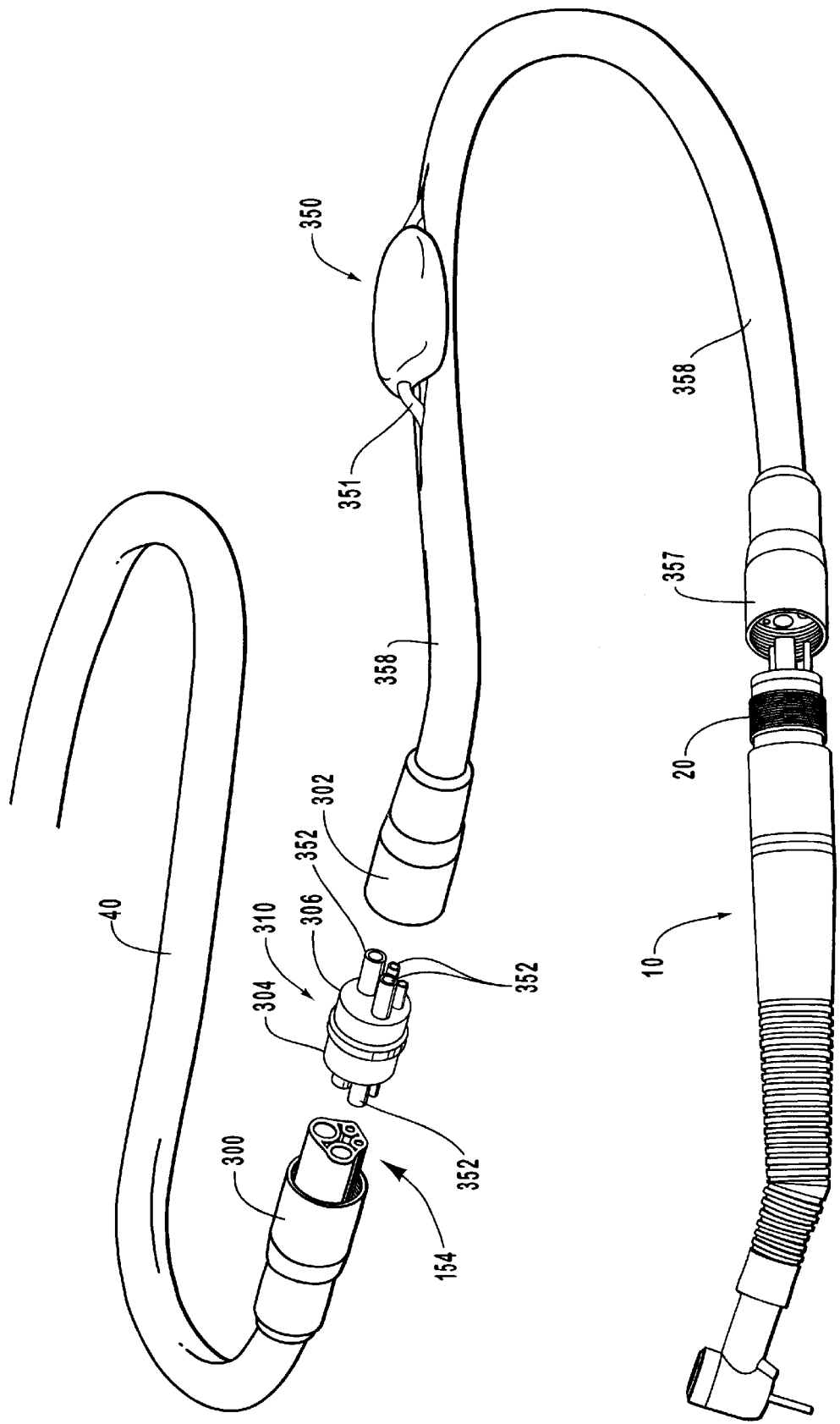
FIG. 3A shows a perspective view of a dental handpiece to be connected to one end of a filter tubing and a connector configured at both ends for compression fitting to tubing.

Coupler lumens have one connector at each end. For example, in the embodiment shown in FIG. 2, connectors 152 are smooth and featureless straight tubular extensions, extending from coupler body 110, and configured to be received by corresponding tubing lumens 154 at non-circular tubing end 35 and at non-circular filter tubing end 54. Similarly, connectors 352 shown in FIG. 3A are also smooth and featureless straight tubular extensions from coupling terminals 304 and 306 in coupler body 310. Instead of straight, featureless ends, embodiments of connectors of couplers of this invention can have other known features that cooperate to provide a leak-proof connection with corresponding tubing lumens, such as the flared ends of connectors 452 shown in FIGS. 3B and 6. Still in other embodiments of the present invention, the coupler lumen ends are flush with the sides of the coupler body, such as coupler lumen ends 552 shown in FIG. 5. More particularly, in the embodiment shown in FIG. 5 the coupler lumen connectors are merely the coupler lumen ends that are configured for receiving corresponding tubing elements 554 that extend from the tubing ends.

Coupler lumens with any one of the different examples of connectors as described hereinabove and equivalents thereof are additional examples of means for establishing fluid communication according to the present invention.

Coupler lumens according to this invention can be embodied by conduit elements that are encased within the coupler body, or they can be embodied by conduit elements in the form of passages formed within the coupler body itself. Furthermore, such conduit elements can be made of the same material as the coupler body or they can be made of a different material.

Embodiments of the coupler body of this invention can also comprise one or more alignment elements, which have receiving or protruding features for engaging corresponding protruding or receiving features, respectively, at the ends of the pieces of tubing to be connected. For example, alignment cavity 156 in the embodiment shown in FIGS. 2 and 3B can be used for receiving a prong (not shown) extending from non-circular filter tubing end 54 for alignment purposes.

Figure 6:
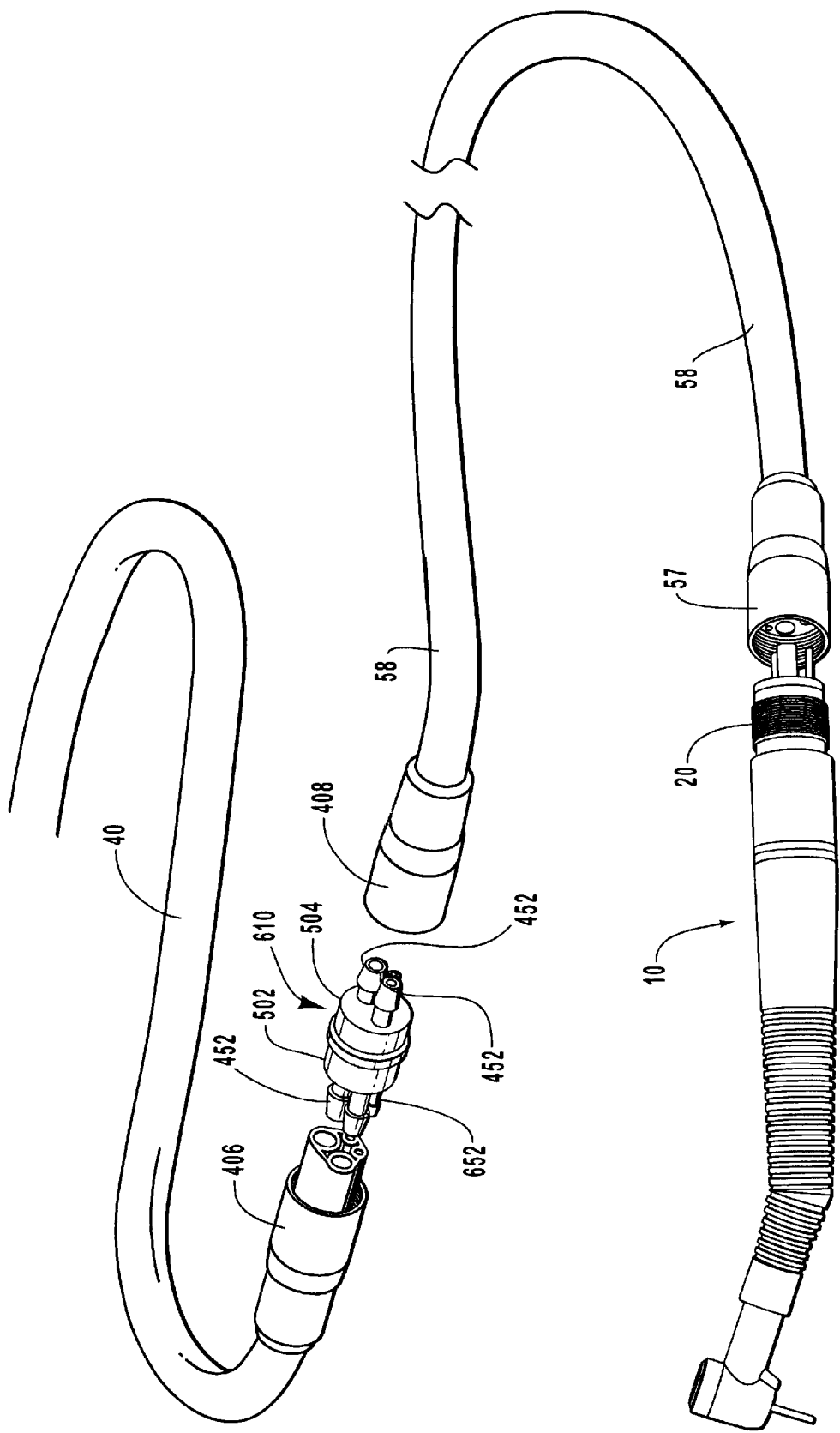
FIG. 6 shows another embodiment of a coupler with compression fitting coupling terminals, flared connectors, and a blind end for one of the connectors.

Any number of the coupler lumens in embodiments of the present invention can have an open end for coupling with a corresponding tubing lumen, and have a closed opposite end. Such coupler lumens are referred to as a blind ports. FIG. 6 shows an embodiment of a coupler with a blind port for coupler lumen 652. This feature can be useful when an embodiment of the coupler of this invention is used for connecting two pieces of tubing that have different numbers of lumens. For example, four coupler lumens 452 extend from coupling terminal 502 whereas only three coupler lumens extend from coupling terminal 504 in the embodiment shown in FIG. 6. Coupler lumen 652 in this embodiment is provided with a blind end.

Figure 3B:
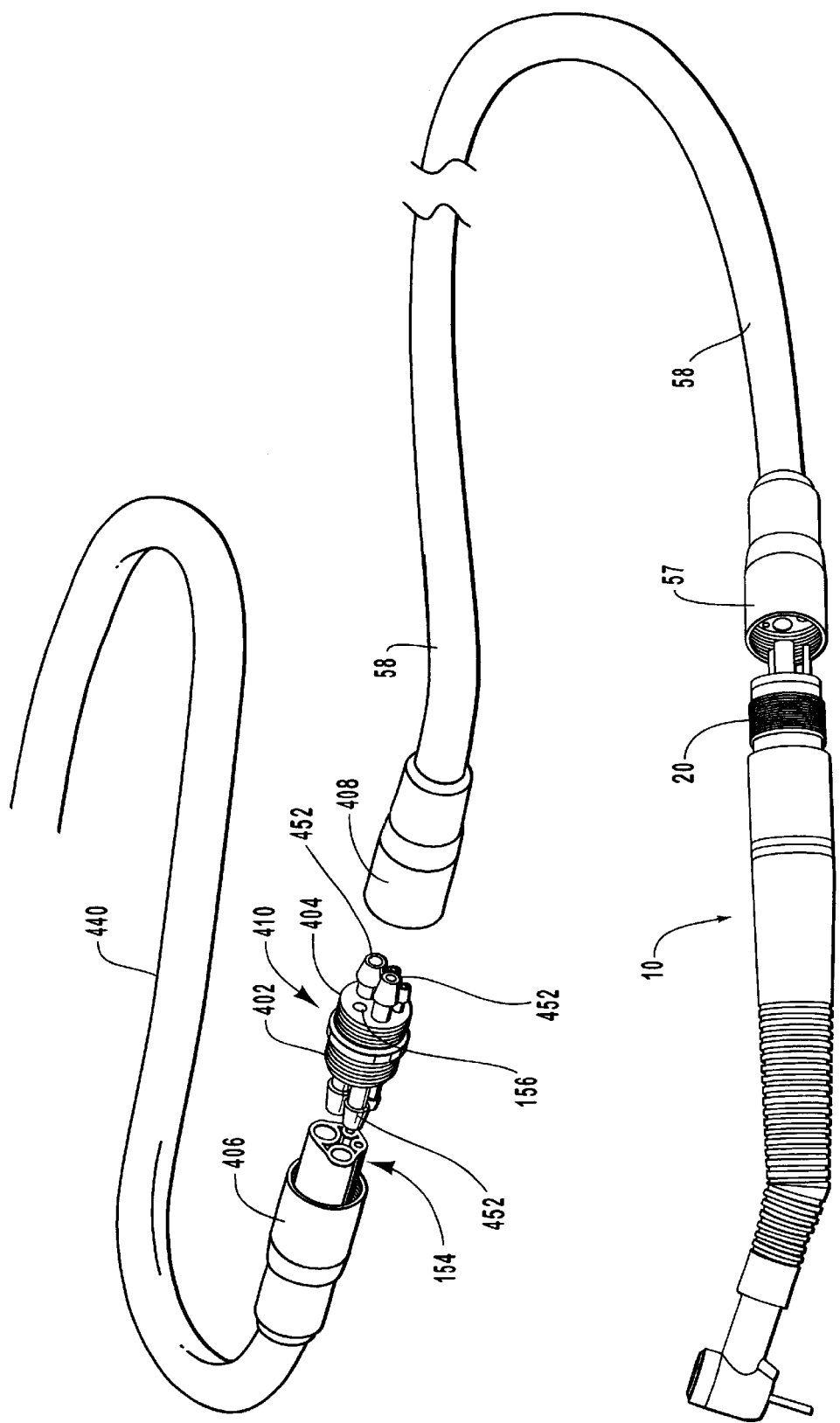
FIG. 3B shows a perspective view of a dental handpiece and a connector configured at both ends for threaded engagement to tubing.
Figure 5:
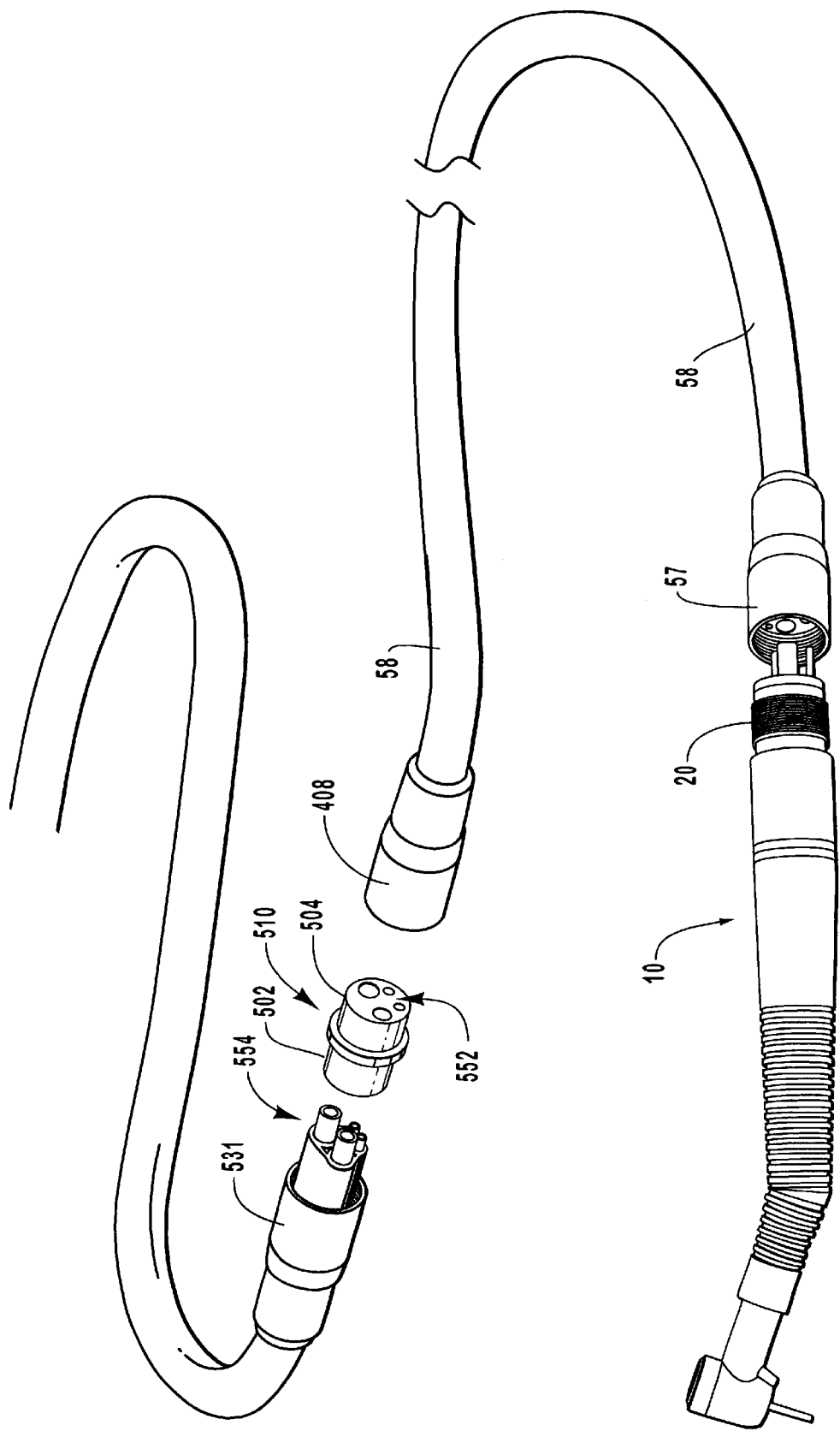
FIG. 5 shows another embodiment of a coupler with compression fitting coupling terminals and receiving connectors.

Embodiments of coupling terminals of this invention can have a variety of shapes and attachment features. For example, coupling terminals 304 and 306 have generally circular cross sections that are configured for compression fitting with receiving compression fitting assemblies 300 and 302, respectively. As known in the art, compression fitting can be more effectively achieved with the aid of mating features in the compression fitting assemblies and coupling terminals, such as interlocking features, snap fastening features or other equivalent features. Coupling terminals 112 and 114 also have a generally circular cross section, but these terminals are configured for threadable engagement with receiving threaded assemblies 31 and 55, respectively. Coupling terminals 304, 306 shown in FIG. 3A and coupling terminals 502, 504 shown in FIGS. 5 and 6 are additional examples of coupling terminals that are configured for compression fitting. Coupling terminals 402, 404 shown in FIG. 3B are additional examples of coupling terminals that are configured for threadable engagement. Features including threads and compression fittings in the coupling terminals of couplers according to this invention are examples of embodiments of means for detachably engaging a coupling terminal with a tubing attachment element.

In addition to the attachment features described in relation to the coupling terminals 112, 114, 304, 306, 502, and 504, other combinations of the same or equivalent engagement features are within the scope of this invention.

Figure 4A:
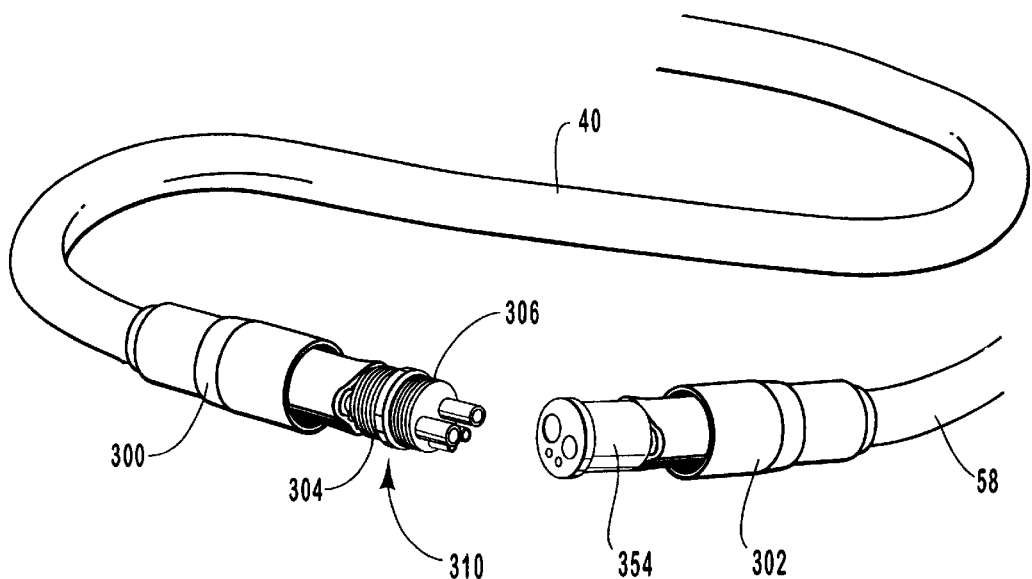
FIG. 4A shows a coupler that is connected at one end to the end of a tubing and is arranged to be connected at its other end with another tubing.
Figure 4B:
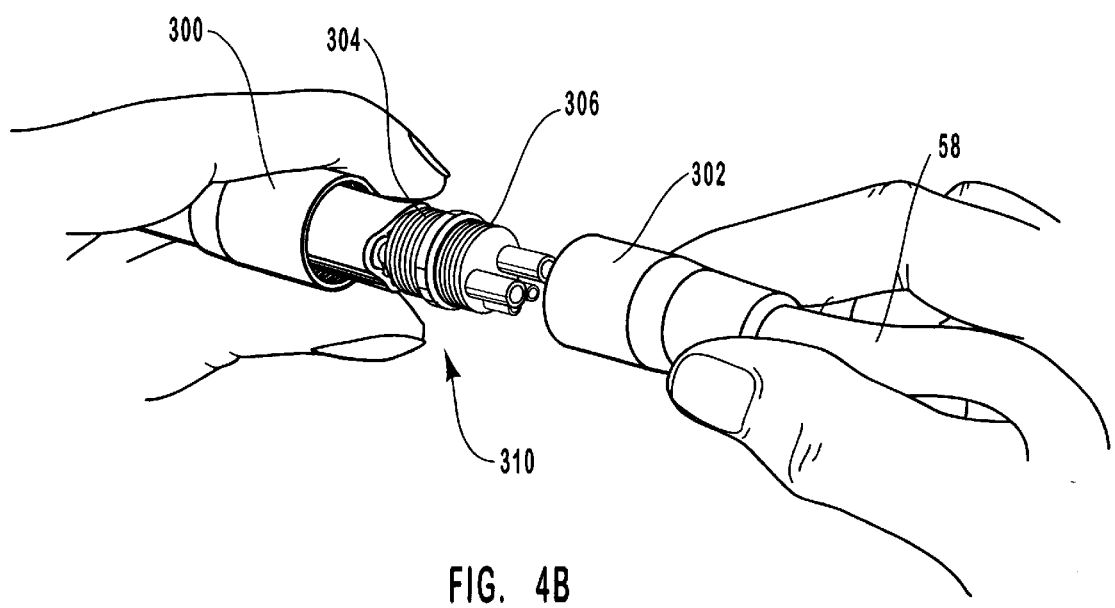
FIG. 4B shows a perspective view of a connector and two tubings in a partially connected configuration.
Figure 4C:
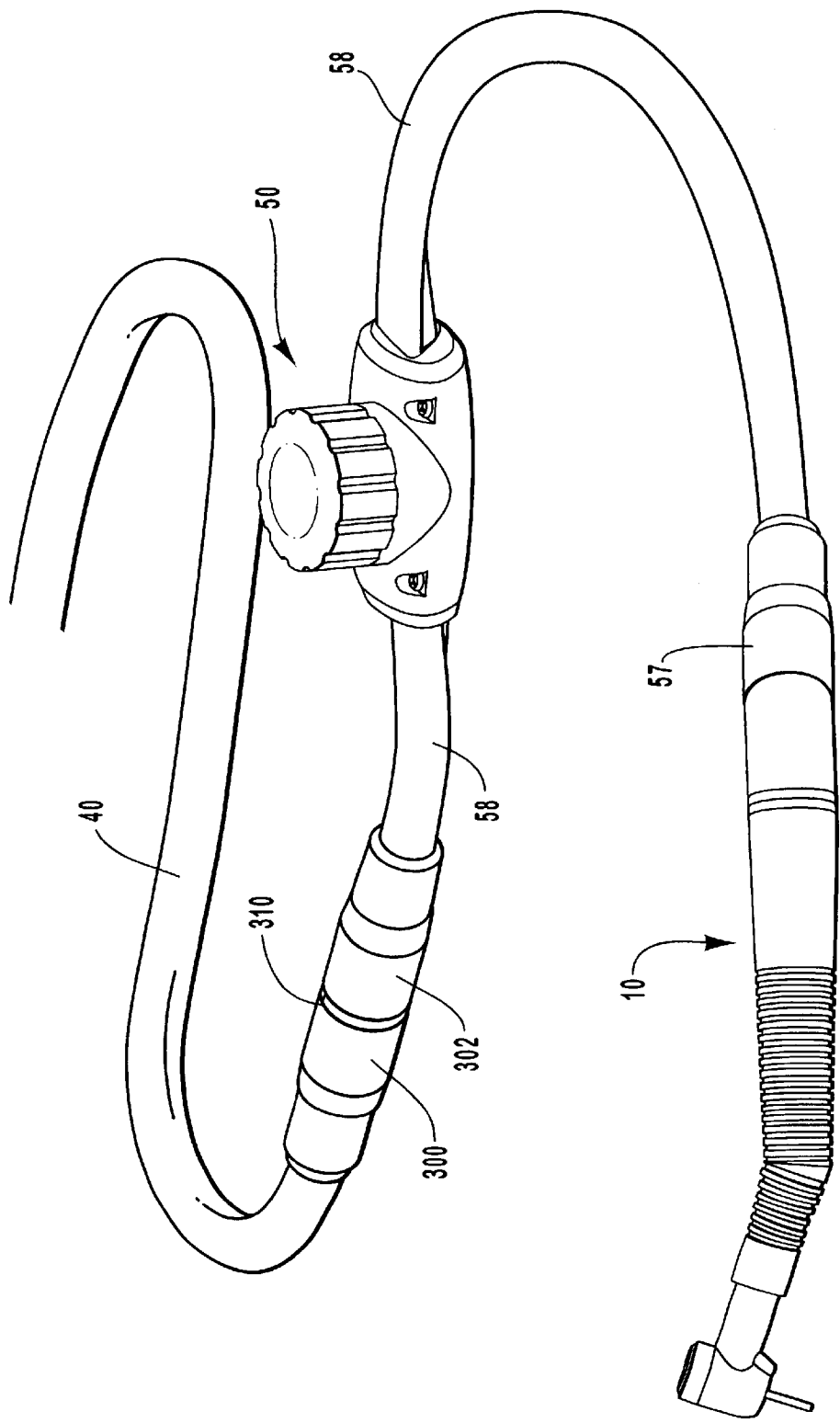
FIG. 4C shows a perspective view of a connector and two tubings in a fully connected configuration.

FIGS. 4A, 4B and 4C show different stages in the assembling of an embodiment 310 of a coupler of this invention with the ends of two pieces of tubing 40 and 58. In the embodiment shown in FIGS. 4A and 4B, all the tubing assemblies 300 and 302 are threaded receiving assemblies and coupling terminals 304 and 306 are threaded coupling terminals. Tubing end 354 shown in FIG. 4A exemplifies any one of the ends of tubings with which embodiments of the present invention can be used, such as an auxiliary device tubing end, more particularly an end of a filter tubing, and the end of an extension tubing. The embodiment shown in FIG. 4C depicts tubings 40 and 58 connected with connector 310 in a fully assembled configuration for operating dental handpiece 10. This embodiment is also representative of a fully assembled configuration with a threaded coupler.

FIG. 3A depicts another embodiment of an auxiliary device 350 that can embody a filter or a reservoir for a substance that is to be mixed with any one of the fluids circulating within any of the tubing lumens, such as lumen 351, within tubing 358. Auxiliary device 350 can also embody a device for the physical or chemical treatment of any one of the fluids that circulate within any of such tubing lumens.

Like filter 50 and corresponding filter tubing 58, auxiliary device 350 and corresponding auxiliary tubing 358 are preferably placed so that auxiliary tubing assembly 357 engages threaded attachment unit 20. However, embodiments of the coupler of this invention can be used to connect auxiliary devices and their tubing portions at any other location between the dental handpiece and the source of the fluid or fluids used to operate the dental handpiece's drill.

FIG. 3B shows an embodiment of a coupler 410 with threaded coupling terminals 402, 404. This coupler is aligned in FIG. 3B with threaded assembly 406 of tubing 440 and threaded assembly 408 of tubing 58, which generically represents an additional portion of tubing, such as an extension tubing or an auxiliary device tubing, that is to be connected by assembly 57 at one of its ends to threaded attachment unit 20 of handpiece 10.

Although the claims appended hereinbelow refer to elements of embodiments of this invention with ordinal terms such as "first" and "second", such ordinal terms are merely used for labelling purposes, and they do not attach specific limitations to the recited elements.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A coupler for dental handpiece tubings which each have a plurality of lumens and which each have ends adapted for coupling with the coupler via tubing assemblies, comprising:

(a) a body having a first coupling terminal opposite to a second coupling terminal, said first coupling terminal having means for detachably engaging a first tubing assembly of a first tubing, said second coupling terminal having means for detachably engaging a second tubing assembly of a second tubing; and (b) a plurality of coupler lumens extending through said body, each coupler lumen having a first connector opposite from a second connector, said connectors extending from the body for detachable leak-proof fluid communication between said tubing lumens and said coupler lumens.

2. A coupler as recited in claim 1, wherein at least one of said engaging means of said first and second coupling terminals includes threads.

3. A coupler as recited in claim 1, wherein at least one of said engaging means of said first and second coupling terminals is a compression fitting.

4. A coupler as recited in claim 1, wherein said body has a circular cross-section.

5. A coupler as recited in claim 1, wherein said coupler lumens are generally straight.

6. A coupler as recited in claim 1, wherein said first connectors have flared ends.

7. A coupler as recited in claim 1, wherein said second connectors have ends that are straight, tubular and non-flared.

8. A coupler as recited in claim 1, wherein said first connectors have flared ends and wherein said second connectors have ends that are straight, tubular and non-flared.

9. A coupler as recited in claim 1, wherein said first connectors and said second connectors have ends that are straight, tubular and non-flared.

10. A coupler as recited in claim 1, wherein said first connectors and said second connectors have ends that are flared.

11. A coupler as recited in claim 1, wherein said plurality of coupler lumens comprises four coupler lumens.

12. A coupler as recited in claim 11, wherein two of said coupler lumens have larger diameters than the other two of said coupler lumens.

13. A coupler for dental handpiece tubings which each have a plurality of lumens for coupling with the coupler via threaded tubing assemblies, comprising:
(a) a body with a first threaded coupling terminal and to a second threaded coupling terminal, said first coupling terminal being opposite to said second coupling terminal, wherein said first coupling terminal is configured for detachable threaded engagement with a first tubing assembly of a first tubing by receiving the first tubing assembly onto and around the first coupling terminal, and said second coupling terminal is configured for detachable threaded engagement with a second tubing assembly of a second tubing by receiving the second tubing assembly onto and around the second coupling terminal; and
(b) a plurality of coupler lumens extending through said body, each coupler lumen having a first connector opposite from a second connector, and wherein said connectors extend from the body for detachable leak-proof fluid communication between said tubing lumens and said coupler lumens.

14. A coupler as recited in claim 13, wherein at least one of said coupler lumens is adapted for the transmission of a specialized element signal.

15. A coupler as recited in claim 13, wherein said first connectors have flared ends.

16. A coupler as recited in claim 13, wherein said second connectors have ends that are straight, tubular and non-flared.

17. A coupler as recited in claim 13, wherein said first connectors have flared ends and wherein said second connectors have ends that are straight, tubular and non-flared.

18. A coupler as recited in claim 13, wherein said first connectors and said second connectors have ends that are straight, tubular and non-flared.

19. A coupler as recited in claim 13, wherein said first connectors and said second connectors have ends that are flared.

20. A coupler as recited in claim 13, wherein said coupler has four coupler lumens.

21. A coupler as recited in claim 20, wherein two of said coupler lumens have larger diameters than the other two of said coupler lumens.

22. A coupler for dental handpiece tubings which each have a plurality of lumens and which each have ends adapted for coupling with the coupler via threaded tubing assemblies, comprising:
(a) a body with a first threaded coupling terminal and a second threaded coupling terminal, said first coupling terminal being opposite to said second coupling terminal, wherein said first coupling terminal is configured for detachable threaded engagement with a first tubing assembly of a first tubing by receiving the first tubing assembly onto and around the first coupling terminal, and said second coupling terminal is configured for detachable threaded engagement with a second tubing assembly of a second tubing by receiving the second tubing assembly onto and around the second coupling terminal; and
(b) a plurality of coupler lumens, each coupler lumen having a first connector and a second connector, said first connector being opposite to said second connector, wherein said plurality of coupler lumens extend through said body and said connectors extend from the body, and wherein each first connector has a flared end configured for detachable lead-proof engagement with a tubing lumen of said first tubing, and each second connector is straight, tubular and non-flared for insertion into a tubing end adapter for detachable leak-proof engagement with the tubing end adapter and for fluid communication with a tubing lumen of said second tubing, such that leak-proof fluid communication between said tubing lumens is established through said coupler lumens.

23. A coupler as recited in claim 22, wherein said coupler lumens are generally straight.

24. A coupler as recited in claim 22, wherein at least one of said coupler lumens is adapted for the transmission of water.

25. A coupler as recited in claim 22, wherein at least one of said coupler lumens is adapted for the transmission of a gas.

26. A coupler as recited in claim 22, wherein at least one of said coupler lumens is adapted for the transmission of a specialized element signal.

27. A coupler as recited in claim 22, wherein said coupler has four coupler lumens.

28. A coupler as recited in claim 27, wherein two of said coupler lumens have larger diameters than the other two of said coupler lumens.

29. A dental handpiece coupling system, comprising:
(a) a first dental handpiece tubing which has a plurality of lumens, wherein the first tubing has a first tubing assembly slidably mounted onto an end,
(b) a second dental handpiece tubing which has a plurality of lumens, wherein the second tubing has a second tubing assembly slidably mounted around a tubing end adapter attached to an end of said second tubing,
(c) a coupler for the dental handpiece tubings, said coupler having
(i) a coupler body having a first coupling terminal opposite to a second coupling terminal, said first coupling terminal having means for detachably engaging the first tubing assembly and said second coupling terminal having means for detachably engaging the second tubing assembly, and (ii) a plurality of coupler lumens extending through said body, each of said coupler lumens having a first and a second connector extending from the body that are opposite to each other, and wherein each said first connector has a flared end configured for detachable leak-proof engagement with one of the tubing lumens of said first tubing, and wherein each second connector is straight, tubular and non-flared for insertion into the tubing end adapter for detachable leak-proof engagement with the tubing end adapter and for fluid communication with the tubing lumens of said second tubing, such that leak-proof fluid communication between said tubing lumens is established through said coupler lumens.

30. A dental handpiece coupling system as recited in claim 29, wherein said second tubing is an extension tubing.

31. A dental handpiece coupling system as recited in claim 29, wherein said first tubing is an auxiliary device tubing that is connected to an auxiliary device.

32. A dental handpiece coupling system as recited in claim 31, wherein said auxiliary device is a device for the treatment of a fluid to be circulated through said tubing lumen.

33. A dental handpiece coupling system as recited in claim 32, wherein said device for the treatment of a fluid is a filter.

34. A dental handpiece coupling system as recited in claim 29, wherein at least one of said first and second coupling terminals is threaded.

35. A dental handpiece coupling system as recited in claim 29, wherein at least one of said first and second coupling terminals is configured for compression fitting.

36. A coupler as recited in claim 29, wherein said coupler has four coupler lumens extending through said body.

37. A coupler as recited in claim 36, wherein two of said coupler lumens have larger diameters than the other two of said coupler lumens.

38. A dental handpiece coupling system, comprising:
(a) a first dental handpiece tubing which has a plurality of lumens, wherein the first tubing has a first threaded tubing assembly slidably mounted onto an end,
(b) a second dental handpiece tubing which has a plurality of lumens, wherein the second tubing has a second threaded tubing assembly slidably mounted around a tubing end adapter attached to an end of said second tubing,
(c) a coupler for the dental handpiece tubings, said coupler having
(i) a body with a first coupling terminal and a second coupling terminal, said first coupling terminal being opposite to said second coupling terminal, wherein said first coupling terminal is configured for detachable threaded engagement with the first tubing assembly of the first tubing, and said second coupling terminal is configured for detachable threaded engagement with the second tubing assembly of the second tubing, and
(ii) a plurality of coupler lumens extending through said body, each of said coupler lumens having a first and a second connector extending from the body that are opposite to each other, and wherein each said first connector has a flared end configured for detachable leak-proof engagement with one of the tubing lumens of said first tubing, and wherein each second connector is straight, tubular and non-flared for insertion into the tubing end adapter for detachable leak-proof engagement with the tubing end adapter and for fluid communication with the tubing lumens of said second tubing, such that leak-proof fluid communication between said tubing lumens is established through said coupler lumens.

39. A dental handpiece coupling system as recited in claim 38, wherein said second tubing is an extension tubing.

40. A dental handpiece coupling system as recited in claim 38, wherein said first tubing is an auxiliary device tubing that is connected to an auxiliary device.

41. A dental handpiece coupling system as recited in claim 40, wherein said auxiliary device is a device for the treatment of a fluid to be circulated through said tubing lumen.

42. A dental handpiece coupling system as recited in claim 41, wherein said device for the treatment of a fluid is a filter.

* * * * *

UNITED STATES PATENT AND TRADEMARK OFFICE
CERTIFICATE OF CORRECTION

PATENT NO. : 6,270,344 B1
DATED : August 7, 2001
INVENTOR(S) : Dan E. Fischer, Bruce S. McLean and Richard Kim Bleiweiss It is certified that error appears in the above-identified patent and that said Letters Patent is hereby corrected as shown below:

Title page,
ABSTRACT, after "plurality of" change "lumen" to -- lumens --

Column 10,
Line 31, change "lead-proof" to -- leak-proof --

Signed and Sealed this

Sixteenth Day of April, 2002

*Attest:*

*Attesting Officer*

JAMES E. ROGAN
*Director of the United States Patent and Trademark Office*